(12) United States Patent
Jan et al.

(10) Patent No.: US 9,926,515 B2
(45) Date of Patent: Mar. 27, 2018

(54) CONTACT LENS CARE SOLUTION

(71) Applicant: BenQ Materials Corporation, Taoyuan (TW)

(72) Inventors: Fan-Dan Jan, Taoyuan (TW); Bo-Ching Lin, Taoyuan (TW); Min-Chun Chung, Taoyuan (TW)

(73) Assignee: BENQ MATERIALS CORPORATION, Taoyuan (TW)

( * ) Notice: Subject to any disclaimer, the term of this patent is extended or adjusted under 35 U.S.C. 154(b) by 0 days.

(21) Appl. No.: 15/397,642

(22) Filed: Jan. 3, 2017

(65) Prior Publication Data
US 2017/0298296 A1 Oct. 19, 2017

(30) Foreign Application Priority Data

Apr. 19, 2016 (TW) .............................. 105112069 A
Sep. 1, 2016 (TW) .............................. 105128026 A

(51) Int. Cl.
| | |
|---|---|
| *C11D 3/00* | (2006.01) |
| *A61L 12/14* | (2006.01) |
| *C11D 3/20* | (2006.01) |
| *C11D 3/37* | (2006.01) |

(52) U.S. Cl.
CPC ............ *C11D 3/0078* (2013.01); *A61L 12/14* (2013.01); *A61L 12/141* (2013.01); *C11D 3/2065* (2013.01); *C11D 3/3773* (2013.01)

(58) Field of Classification Search
None
See application file for complete search history.

(56) References Cited

U.S. PATENT DOCUMENTS

| | | | | |
|---|---|---|---|---|
| 2008/0096966 | A1* | 4/2008 | Burke | .................. A61K 9/0048 514/561 |
| 2010/0280204 | A1* | 11/2010 | Ishii | ...................... C07C 231/08 526/307.1 |
| 2011/0028477 | A1* | 2/2011 | Aleo | .................... A61K 9/0048 514/236.2 |

* cited by examiner

*Primary Examiner* — Robert A Wax
*Assistant Examiner* — Melissa S Mercier
(74) *Attorney, Agent, or Firm* — Chun-Ming Shih

(57) ABSTRACT

The invention is related to a contact lens care solution comprising a buffer solution, a chelating agent, a surfactant and a wetting agent, wherein the wetting agent comprises 100 parts by weight of glycerol, 0.5 to 40 parts by weight of vinylacetamide-containing polymer and 5 to 40 parts by weight of alginic acid.

12 Claims, No Drawings

CONTACT LENS CARE SOLUTION

This application claims the benefit of TW application No. 105112069, filed on Apr. 19, 2016, and the benefit of TW application No. 105128206, filed on Sep. 1, 2016, and the entireties of which are incorporated by reference herein.

BACKGROUND OF THE INVENTION

Field of the Invention

The present disclosure relates to a contact lens care solution and particularly, relates to a contact lens care solution providing cleaning ability with enhancing wetting ability to the contact lenses.

Description of the Related Art

When wearing contact lenses, protein and/or lipid deposits will accumulate on contact lenses. In the case of wearing contact lenses for a certain time, the wearer's eyes are susceptible to dry, thus reducing wear comfort. In addition, the protein deposits gradually accumulated on the lenses to cause the wearer eyes discomfort, such as corneal congestion, conjunctivitis, corneal neovascularization, corneal ulcers and other issues to affect the eye sight and more seriously, cause infection. Thus, the daily cleaning of the contact lenses is very important.

For effectively cleaning the contact lenses, the contact lenses are immersed in the care solution for a period of time to remove the protein and/or lipid deposits thereon. However, the contact lenses will absorb the components of the care solution after immersing for a period of time, the absorbed components may cause the wearer eyes discomfort and irritation. Thus, some agents, such as demulcents, wetting agents, tonic agent and the likes, are added to the contact lens care solution to relief the wearers' discomfort. It has been proposed to added 0.2 to 1.5 percent by weight of glycerol as a wetting agent in the care solution.

SUMMARY OF THE INVENTION

To solve the above mentioned problem, the present invention provides a contact lenses care solution for cleaning and wetting the contact lenses. The present contact lens care solution comprises a novel wetting agent comprising vinylacetamide-containing polymer, alginic acid and glycerol. This wetting agent is biocompatible and low-cytotoxic. After using the present contact lens care solution to clean the contact lens, the symptoms of ocular discomfort and irritation can be significantly relieved.

This disclosure is to provide a care solution for contact lenses. The contact lens care solution comprises a buffer solution, a chelating agent, a surfactant and a wetting agent. The wetting agent comprises 100 parts by weight of glycerol, 0.5 to 40 parts by weight of vinylacetamide-containing polymer and 5 to 40 parts by weight of alginic acid.

The wetting agent used in the present contact lens care solution comprises a specific ratio of vinylacetamide-containing polymer, alginic acid and glycerol. In one aspect of the present invention, the wetting agent used in the present invention provides good biocompatibility, low cytotoxicity and the ability to be aptly adsorbed to the contact lenses. Furthermore, it is know that the glycerol used in the contact lens solution absorbed on the contact lens may absorb the moisture of the eye. The low addition amount of glycerol in the present wetting agent can be lowered the discomfort caused by the glycerol.

The wetting agent of the present contact lens care solution comprises 1 to 35 parts by weight of vinylacetamide-containing polymer and 10 to 35 parts by weight of alginic acid per 100 parts by weight glycerol.

The vinylacetamide-containing polymer suitable used in the wetting agent of the present contact lens care solution can be vinylacetamide homopolymer or vinylacetamide copolymer. The vinylacetamide homopolymer is polymerized by vinylacetamide monomers. The vinylacetamide copolymer is polymerized by vinylacetamide monomers and other monomers with cross-linkable functional groups. The other monomer with cross-linkable functional groups can be for example sodium acrylate.

In one preferred embodiment of the present invention, the addition amount of the wetting agent in the present contact lens care solution can be in the range of about 0.01 parts by weight to 0.20 parts by weight per 100 parts by weight of buffer solution and preferably can be 0.04 parts by weight to 0.14 parts by weight.

In one preferred embodiment of the present invention, the wetting agent of the present contact lens care solution can further comprise a hyaluronic acid.

In one preferred embodiment of the present invention, the wetting agent of the present contact lens care solution can be further added 20 to 70 parts by weight of hyaluronic acid.

In one preferred embodiment of the present contact lens care solution of the present invention, the components of the wetting agent can be added into the buffer solution after mixing together or added individually into the buffer solution.

In one preferred embodiment of the present invention, the buffer solution in the present contact lens care solution is a solution of deionic water with at least one component selected from the group consisting of sodium chloride, boric acid and the salt thereof, phosphoric acid and the salt thereof, nitric acid and the salt thereof, tartaric acid and the salt thereof, carbonic acid and the salt thereof, bicarbonates, lactic acid and the salt thereof, citric acid and the salt thereof, acetic acid and the salt thereof, polyol and the derivatives thereof, sulfonic acid and the derivatives thereof and the combinations thereof. The salts can be alkali metal salts, such as sodium salt or potassium salt, but not limited thereto.

In one preferred embodiment of the present invention, the chelating agent suitable used in the present contact lens care solution can be selected from the group consisting of ethylenediaminetetraacetic acid (EDTA) and the salt thereof, polyphosphates and the salt thereof, succinic acid and the salt thereof, tartaric acid and the salt thereof, tetraacetic acid and the salt thereof. The salts can be alkali metal salts, such as sodium salt or potassium salt, but limited thereto.

In one preferred embodiment of the present invention, the suitable surfactant used for present contact lens care solution is selected from the group consisting of poloxamer, poloxamer derivatives, poloxamine, poloxamine derivatives, sodium citrate, cationic surfactant and the like.

In one preferred embodiment of the present invention, the addition amount of the chelating agent for the present contact lens care solution is between about 0.01 parts by weight to 1.0 parts by weight per 100 parts by weight of buffer solution and preferably is between about 0.02 parts by weight to 0.05 parts by weight.

In one preferred embodiment of the present invention, the addition amount of the surfactants suitably used in the present contact lens care solution is between about 0.1 parts by weight to 1.0 part by weight per 100 parts by weight of buffer solution and preferably is between 0.6 parts by weight to 0.7 parts by weight.

In one preferred embodiment of the present invention, the present contact lens care solution can further comprise disinfecting agents, antioxidants, thickeners, tonicity adjusting agents, lubricants or the combination thereof.

In one preferred embodiment of the present invention, the suitable disinfecting agent used for the present contact lens care solution is selected from the group consisting of polyhexamethylene biguanide (PHMB), the water-soluble salts of PHMB, polyaminopropyl biguanide (PAPB), the water-soluble salts of polyaminopropyl biguanide, protamine sulfate and melittin.

In one preferred embodiment of the present invention, the addition amount of the disinfecting agent for the present contact lens care solution is between about 0.0001 parts by weight to 0.1 parts by weight per 100 parts by weight of buffer solution and preferably is between about 0.0001 parts by weight to 0.03 parts by weight.

In one preferred embodiment of the present invention, the antioxidant suitable used in the contact lens care solution can be selected from the group consisting of sulfite, ascorbate, butylated hydroxyanisole (BHA), butylated hydroxytoluene (BHT), astaxanthin and vitamin C and the combination thereof.

In one preferred embodiment of the present invention, the addition amount of the antioxidant of the present contact lens care solution can be in the range of about 0.001 parts by weight to 0.1 parts by weight per 100 parts by weight of buffer solution.

DETAILED DESCRIPTION OF THE INVENTION

The above-mentioned and other objects, features and advantages of the present invention will become more apparent in light of the following detailed description taken together with the examples.

In an aspect of the present invention, the present invention is to provide a care solution for contact lenses comprising a buffer solution, a chelating agent, a surfactant and a wetting agent. The wetting agent comprises a vinylacetamide-containing polymer, an alginic acid and glycerol, wherein the wetting agent comprises 100 parts by weight of glycerol, 0.5 to 40 parts by weight of vinylacetamide-containing polymer and 5 to 40 parts by weight of alginic acid.

The present invention provides a contact lenses care solution for cleaning and wetting the contact lenses. The present contact lens care solution comprises a novel wetting agent comprising vinylacetamide-containing polymer, alginic acid and glycerol. This wetting agent is biocompatible and low-cytotoxic. For relief the symptoms of irritation and red eyes. After using the present contact lens care solution to clean the contact lens, the wetting ability of the contact lens is improved for alleviating the discomfort caused by the eye dryness.

The wetting agent used in the present contact lens care solution comprises a specific ratio of vinylacetamide-containing polymer, alginic acid and glycerol. In one aspect of the present invention, the wetting agent used in the present invention provides a good biocompatibility, low cytotoxicity and the ability to be adsorbed to the contact lenses. Furthermore, due to the low addition amount of glycerol in the present wetting agent, the discomfort caused by the glycerol in the wetting film formed all over the contact lenses by the care solution to absorb the moisture of the eye can be lowered.

The addition amount of the wetting agent in the present contact lens care solution can be in the range of about 0.01 parts by weight to 0.20 parts by weight per 100 parts by weight of the buffer solution and preferably can be in the range of about 0.04 parts by weight to 0.14 parts by weight.

The vinylacetamide-containing polymer suitable used in the wetting agent of the present contact lens care solution can be vinylacetamide homopolymer orvinylacetamide copolymer. The vinylacetamide homopolymer is polymerized by vinylacetamide monomers, such as Product GE-191 of SHOWA DENKO (Japan) in the Product Nos. GE-191-053, GE-191-103, GE-191-104GE-191-107 or GE-191-108, but not limited thereto. The vinylacetamide copolymer is polymerized by vinylacetamide monomers and other monomers with cross-linkable functional groups. The other monomer with cross-linkable functional groups can be for example sodium acrylate. The vinylacetamide copolymer can be the product GE-178 of SHOWA DENKO. For the wetting agent can be evenly absorbed on the contact lenses, the viscosity of this vinylacetamide-containing polymer is between 100 mPa·s and 20,000 mPa·s and preferably is between 100 mPa·s and 3,000 mPa·s. The wetting agent in the present contact lens care solution can comprises 1 to 35 parts by weight of vinylacetamide-containing polymer per 100 parts by weight of glycerol.

The alginic acid suitable used in the wetting agent of the present contact lens care solution can be the alginic acid with weight average molecular weight of 1,000 to 30,000 and preferably in the range of 5,000 to 20,000. When the average molecular weight of the alginic acid is not in the range, the protein and/or lipid cleaning ability of the present contact lens care solution will be decreased. The wetting agent in the present contact lens care solution can comprises 10 to 35 parts by weight of alginic acid per 100 parts by weight glycerol.

Furthermore, the present contact lens care solution can further comprise a hyaluronic acid.

The hyaluronic acid suitably used in the wetting agent of the present contact lens care solution is the hyaluronic acid with weight average molecular weight ranged between 100,000 to 8,000,000 and preferably is between 100,000 to 1,300,000. If the average molecular weight of the hyaluronic acid is not in the range, the cleaning ability of the contact lens care solution will be decreased. The addition amount of the hyaluronic acid to the wetting agent can be in the range of 20 to 70 parts by weight, and preferably in the range of 20 to 67 parts by weight.

The components of the wetting agent of the present contact lens care solution can be added into the buffer solution after thoroughly mixing or can be individually added into the buffer solution.

The buffer solution used in the contact lens care solution is for maintaining the pH of contact lens care solution within a suitable range, such as in an acceptable range of 6 to 8. Because the contact lens care solution will be absorbed on the contact lenses, the pH of the contact lens care solution is desired to be close to physiologic pH value 7.4 to enhance the eye comfort. In one preferred embodiment of the present invention, the buffer solution of the present contact lens care solution comprises water, sodium chloride, boric acid and the salt of boric acid.

The buffer solution suitably used in the present contact lens care solution can be any physiologic compatible buffer solution commonly used in the related field, such as borates, phosphates, citrate, boric acid, carbonates and acetates and the like. The salts can be alkali metal salts, such as sodium salt or potassium salt. The concentration of the salts in the buffer solution is between 0.001 wt % and 5 wt %.

The chelating agent suitably used in the present contact lens care solution can be ethylenediaminetetraacetic acid (EDTA) and the salt thereof, polyphosphates and the salt thereof, succinic acid and the salt thereof, tartaric acid and the salt thereof, tetraacetic acid and the salt thereof. The salt of acid can be metal salts, such as, for example, sodium salts or potassium salts. The addition amount of the chelating agent is about 0.01 parts by weight to 1.0 parts by weight per 100 parts by weight of buffer solution, and preferably is about 0.02 parts by weight to 0.05 parts by weight.

In one preferred embodiment of the present invention, the chelating agent used in the present contact lens care solution is disodium EDTA.

The surfactants suitably used in the present contact lens care solution can be selected from the group consisting of poloxamer, poloxamer derivatives, poloxamine, poloxamine derivatives, sodium citrate and cationic surfactant. Poloxamer can be for example Poloxamer 407, Pluronic® L35, L43, L44, L62, L62D, L62LF, L64, L92, F108, F123, F88, F98, F68, F68LF, F127, F87, F77, P84, P85, P75, P103, P104 or P105. The poloxamer derivative means a poloxamer modified by functional groups. The poloxaminecan be but not limited to Tetronic® 707, 1107, 1307, 908 or 1304. The poloxamine derivative means a poloxamine modified by functional groups. The addition amount of these surfactants is between about 0.1 parts by weight and 1.0 parts by weight per 100 parts by weight of the buffer solution and preferably is between about 0.6 parts by weight to about 0.7 parts by weight.

In one preferred embodiment of the present invention, the surfactant used in the present contact lens care solution is poloxamerand sodiumcitrate.

Furthermore, the present contact lens care solution further comprises a disinfecting agent, antioxidant, thickeners, tonicity adjusting agents, lubricants or the combinations thereof.

The suitable disinfecting agent used for the present invention can be, for example, polyhexamethylene biguanide (PHMB), the water-soluble salts of PHMB, polyaminopropyl biguanide (PAPB), the water-soluble salts of PAPB, protamine sulfate or melittin. The addition amount of the disinfecting agent in the present contact lens care solution is between about 0.0001 parts by weight and 0.1 parts by weight per 100 parts by weight of buffer solution and preferably is between about 0.0001 to 0.03 parts by weight.

The suitable antioxidant can be for example sulfites, ascorbates, butylated hydroxyanisole (BHA), butylated hydroxytoluene (BHT), astaxanthin and vitamin C and the like. The addition amount of the antioxidant suitably used in the present invention is between about 0.001 parts by weight to about 0.1 parts by weight per 100 parts by weight of buffer solution.

The suitable tonicity adjusting agents can be, for example, sodium chloride, potassium chloride or mannitol.

The following examples are provided to further illustrate the present invention. It is to be understood, however, that these examples are for purposes of illustration only and are not intended as a definition of the limits of the invention.
Preparation of Contact Lens Care Solution The detailed compositions for Examples 1 to 8 of the contact lens care solution are listed in Table 1.

EXAMPLE 1

40 parts by weight of water was heated to 50° C. and then 0.001 parts by weight of vinylacetamide-containing polymer of vinylacetamide and sodium acrylate (Product name: adHERO GE167, commercially available from SHOWA DENKO, Japan), 0.1 parts by weight of glycerol, 0.01 parts by weight of sodium alginate (CAS No 9005-38-3, average molecular weight of 222, commercially available from Spectrum Chemical, US) and 0.02 parts by weight of disodium EDTA were added thereafter to generate a mixture. This mixture was continually stirred until the additives were completely dissolved.

Next, The resulted mixture was cooled to room temperature and then 0.6 parts by weight of sodium chloride, 0.05 parts by weight of sodium borate, 0.59 parts by weight of boric acid, 0.6 parts by weight of sodium citrate, 0.1 parts by weight of poloxamer (Product name: Poloxamer 407, CAS No. 9003-11-6, commercially available from Sigma Aldrich, USA) and 60 parts by weight of water were added thereafter. This mixture was continually stirred until the additives were completely dissolved.

0.0001 parts by weight of polyhexamethylene biguanide (PHMB, Brand name: COSMOCIL® CQ, CAS No. 32289-58-0, commercially available from LONZA, Switzerland) was added into the resulted solution and stirred until completely dissolved.

The, the prepared solution with the disinfecting agent was packaged after sterile filtration to complete the preparation of the contact lens care solution.

EXAMPLE 2

The preparation procedures of Example 2 were the same as those used in Example 1, except that the addition amounts of glycerol and poloxamer in Example 2 were different from those in Example 1.

EXAMPLE 3

40 parts by weight of water was heated to 50° C. and then 0.001 parts by weight of vinylacetamide-containing polymer of vinylacetamide and sodium acrylate (Product name: adHERO GE167, commercially available from SHOWA DENKO, Japan), 0.1 parts by weight of glycerol, 0.01 parts by weight of sodium alginate (CAS No 9005-38-3, average molecular weight of 222, commercially available from Spectrum Chemical MFG CORP, US), 0.2 parts by weight of sodium hyaluronate (CAS No. 9067-32-7, average molecular weight of 325,000, commercially available from Carbomer, USA) and 0.02 parts by weight of disodium EDTA were added thereafter. This mixture was continually stirred until the additives were completely dissolved.

Next, the resulted mixture was cooled to room temperature and then 0.6 parts by weight of sodium chloride, 0.05 parts by weight of sodium borate, 0.59 parts by weight of boric acid, 0.6 parts by weight of sodium citrate, 0.1 parts by weight of poloxamer (Product name: Poloxamer 407, CAS No. 9003-11-6, commercially available from Sigma Aldrich, USA) and 60 parts by weight of water were added thereafter. This mixture was continually stirred until the additives were completely dissolved.

0.0001 parts by weight of PHMB (Brand name: COSMOCIL® CQ, CAS No. 32289-58-0, commercially available from LONZA, Switzerland) was added into the resulted solution and stirred until completely dissolved.

EXAMPLE 4

The preparation procedures of Example 4 were the same as those used in Example 3, except that the addition amounts of glycerol, poloxamer and vinylacetamide-containing polymer in Example 3 were different from those in Example 4.

EXAMPLE 5

The preparation procedures of Example 5 were the same as those used in Example 3, except that the addition amounts of glycerol, poloxamer and vinylacetamide-containing polymer in Example 5 were different from those in Example 3.

EXAMPLE 6

The preparation procedures of Example 6 were the same as those used in Example 5, except that the disinfecting agent was protamine sulfate (CAS No. 53594-25-4, commercially available from Sigma Aldrich, USA) and the addition amount of disodium DETA in Example 6.

EXAMPLE 7

The preparation procedures of Example 7 were the same as those used in Example 5, except that the disinfecting agent was melittin (CAS No. 20449-79-0 commercially available from Sigma Aldrich, USA) and the addition amount of disodium DETA in Example 7.

EXAMPLE 8

40 parts by weight of water was heated to 50° C. and then added 0.001 parts by weight of vinylacetamide-containing polymer of vinylacetamide and sodium acrylate (Product name: adHERO GE167, commercially available from SHOWA DENKO, Japan), 0.03 parts by weight of glycerol, 0.01 parts by weight of sodium alginate (CAS No 9005-38-3, average molecular weight of 222, commercially available from Spectrum Chemical, US), 0.01 parts by weight of sodium hyaluronate (CAS No. 9067-32-7, average molecular weight of 325,000, commercially available from Carbomer, USA) and 0.05 parts by weight of disodium EDTA. This mixture was stirred until completely dissolved.

Next, the resulted mixture was cooled to room temperature and then added 0.6 parts by weight of sodium chloride, 0.05 parts by weight of sodium borate, 0.59 parts by weight of boric acid, 0.6 parts by weight of sodium citrate, 0.01 parts by weight of poloxamer (Product name: poloxamer 407, CAS No. 9003-11-6, commercially available from Sigma Aldrich, USA) and 0.001 parts by weight of Astaxanthin (commercially available from Material World Industrial, Taiwan) and then, added 60 parts by weight of water. This mixture was stirred until completely dissolved.

0.0001 parts by weight of PHMB (Brand name: COSMOCIL® CQ, CAS No. 32289-58-0, commercially available from LONZA, Switzerland) was added into the resulted solution and stirred until completely dissolved.

TABLE 1 the composition of the care solutions of Example 1 to Example 8

| | Components | Example (parts by weight) | | | | | | | |
|---|---|---|---|---|---|---|---|---|---|
| | | 1 | 2 | 3 | 4 | 5 | 6 | 7 | 8 |
| Buffer Solution | Sodium borate buffer solution | 100 | 100 | 100 | 100 | 100 | 100 | 100 | 100 |
| Chelating agent | EDTA | 0.02 | 0.02 | 0.02 | 0.02 | 0.02 | 0.05 | 0.05 | 0.05 |
| Surfactant | Sodium citrate | 0.6 | 0.6 | 0.6 | 0.6 | 0.6 | 0.6 | 0.6 | 0.6 |
| | Poloxamer | 0.1 | 0.01 | 0.1 | 0.01 | 0.01 | 0.01 | 0.01 | 0.01 |
| Wetting agent | Glycerol | 0.1 | 0.03 | 0.1 | 0.03 | 0.03 | 0.03 | 0.03 | 0.03 |
| | vinylacetamide-containing polymer | 0.001 | 0.001 | 0.001 | 0.01 | 0.001 | 0.001 | 0.001 | 0.001 |
| | Sodium alginate | 0.01 | 0.01 | 0.01 | 0.01 | 0.01 | 0.01 | 0.01 | 0.01 |
| | Sodium hyaluronate | | | 0.02 | 0.02 | 0.01 | 0.01 | 0.01 | 0.01 |
| Disinfectant | PHMB | 0.0001 | 0.0001 | 0.0001 | 0.0001 | 0.0001 | | | 0.0001 |
| | Protamine sulfate | | | | | | 0.03 | | |
| | Melittin | | | | | | | 0.01 | |
| Anti-oxidant | Astaxanthin | | | | | | | | 0.0001 |

The contact lens care solution obtained from Examples 1 to 8 were conducted the following tests to determine the properties and disinfection abilities. The results are shown in Tables 2 and 3.

Contact Angle Test

Commercial silicone hydrogel contact lenses (Product name: Oasys, commercially available from Johnson & Johnson Medical Taiwan) and commercial hydrogel contact lenses (Product name TICON55, commercially available from St. Shine Optical, Taiwan) respectively immersed in the contact lens care solution of Example 1 to Example 8 for 24 hours and then took out the contact lens for contact angle test.

Determination of Protein Removal

The commercial silicone hydrogel contact lenses (Oasys, commercially available from Johnson & Johnson Vision Care (Taiwan)) and commercial hydrogel contact lenses (TICON55, commercially available from St. Shine Optical, Taiwan) available from market were respectively immersed in 3 ml sterile lysozyme solution in a polypropylene (PP) sample tubes. The PP sample tubes then ware sealed and incubated in an oven maintaining at a constant temperature of 37° C. for 12 hours. The contact lenses were moved out and wiped with paper towels to remove lysozyme solution on the contact lenses. The content of the lysozyme within the remaining solution in the PP sample tubes was determined. The determined value of lysozyme contents were set as W1. The move-out contact lenses were re-immersed in a 3 ml contact lens extracting solution (the acetonitrile vol.: trifluoroacetic acid vol.: water vol.=100:0.2:100) in a PP sample tubes. The sample tubes were shaken in a rotating shaker at temperature of 37° C. for 24 hours. Then, the lenses were moved out and the content of lysozyme within the remaining extracting solution were determined. The values of the lysozyme content obtained were set as W2. The protein removal ratio was calculated by the equation set forth as: [W1/(W1+W2)]*100%.

Determination of Lipid Removal

The commercial silicone hydrogel contact lenses (Oasys, commercially available from Johnson & Johnson Vision Care (Taiwan)) and commercial hydrogel contact lenses (TICON55, commercially available from St. Shine Optical, Taiwan) available from market were respectively immersed in 3 ml sterile cholesterol solution in a polypropylene (PP) sample tubes. The PP sample tubes then were sealed and incubated in an oven maintaining at a constant temperature of 37° C. for 12 hours. The contact lenses were moved out and wiped with paper towels to remove cholesterol solution on the contact lenses. The content of the cholesterol within the remaining solution in the PP sample tubes was determined. The determined value of cholesterol contents were set as P1. The move-out contact lenses were re-immersed in a 2 ml contact lens extracting solution (chloroform vol.: methanol vol.=2:1) in PP sample tubes. The sample tubes were shaken in a rotating shaker at temperature of 37° C. for 24 hours. Then, the lenses were moved out and the content of cholesterol within the remaining extracting solution was determined. The values of the cholesterol content obtained were set P2. The lipid removal ratio as calculated by the equation set forth as: [P1/(P1+P2)]*100%.

Disinfection Test

The commercial silicone hydrogel contact lenses (Oasys, commercially available from Johnson & Johnson Vision Care (Taiwan)) and commercial hydrogel contact lenses (TICON55, commercially available from St. Shine Optical, Taiwan) available from market were respectively determined the disinfection ability according to ISO14729. The test time is lasting for 6 hours and 24 hours. In table 2, the symbol "○" represents that the test result meets the ISO standard and the symbol "×" represents that the result fails to meet the ISO standard.

From the results shown in Table 2, after the silicone hydrogel contact lenses have been immersed in the contact lens care solutions of Example 1 to Example 8, the contact angle were at 10.1° to 15.1°, the protein removal was between 55% to 63.2%, and the lipid removal was between 45.9% to 60.1%.

TABLE 2

The test results of the care solutions of Example 1-Example 8

| Properties | Example | | | | | | | |
|---|---|---|---|---|---|---|---|---|
| | 1 | 2 | 3 | 4 | 5 | 6 | 7 | 8 |
| Silicone hydrogel contact lens | | | | | | | | |
| Contact angle (°) | 10.1 | 11.3 | 11.5 | 12.2 | 14.9 | 14.5 | 15.1 | 14.8 |
| Protein removal (%) | 63.2 | 56.4 | 61.1 | 55.3 | 58.4 | 55.0 | 58.2 | 58.6 |
| Lipid removal (%) | 51.4 | 49.5 | 45.9 | 55.9 | 59.3 | 60.1 | 58.9 | 59.5 |
| Hydrogel contact lens | | | | | | | | |
| Contact angle (°) | 11.3 | 11.5 | 10.5 | 11.5 | 11.8 | 11.2 | 11.2 | 11.7 |
| Protein removal (%) | 49.3 | 56 | 47.7 | 52.8 | 50.0 | 50.1 | 50.5 | 51.1 |
| Lipid removal (%) | 44.4 | 50.5 | 44.9 | 58.5 | 53.1 | 52.8 | 52.9 | 53.2 |

The hydrogel contact lenses were immersed in the contact lens care solution of Example 1 to Example 8, the contact angles of the contact lenses were 10.5° to 11.8°, the protein removal ratios of the contact lenses were 47.7% to 56.0%, the lipid removal of the contact lenses were 44.9% to 58.5%. Thus, the present contact lens care solution, either used with silicone hydrogel contact lenses or hydrogel contact lenses, the contact angles of the lenses after immersed can be maintained less than 15.8°. Thus, the contact lenses can be provided with effective wetting ability. Furthermore, the protein removal and lipid removal of the contact lenses can be more than about 45%.

From the results of the disinfection determination shown in Table 3, the results of the disinfection tests of the contact lens care solution of Example 1 to Example 8 to the *E. coli, Staphylococcus aureus* and *Pseudomonas aeruginosa* all met the ISO standard.

TABLE 3

The disinfection test for the care solutions of Example 1-Example 8

| Disinfection | | Example | | | | | | | |
|---|---|---|---|---|---|---|---|---|---|
| | | 1 | 2 | 3 | 4 | 5 | 6 | 7 | 8 |
| *E. coli* | 6 hours | ○ | ○ | ○ | ○ | ○ | ○ | ○ | ○ |
| | 24 hours | ○ | ○ | ○ | ○ | ○ | ○ | ○ | ○ |
| *Staphylococcus* | 6 hours | ○ | ○ | ○ | ○ | ○ | ○ | ○ | ○ |
| *aureus* | 24 hours | ○ | ○ | ○ | ○ | ○ | ○ | ○ | ○ |
| *Pseudomonas* | 6 hours | ○ | ○ | ○ | ○ | ○ | ○ | ○ | ○ |
| *aeruginosa* | 24 hours | ○ | ○ | ○ | ○ | ○ | ○ | ○ | ○ |

The invention has been described in detail, with reference to certain preferred embodiments, in order to enable the reader to practice the invention without undue experimentation, such description is for illustrative purposes only. However, a person having ordinary skill in the art will readily recognize that many of the components and parameters may be varied or modified to a certain extent without departing from the scope and spirit of the invention, which is set forth in the following claims.

What is claimed is:

1. A care solution for contact lenses comprising:
    a buffer solution;
    a chelating agent;
    a surfactant; and
    a wetting agent comprising 100 parts by weight of glycerol, 0.5 to 40 parts by weight of vinylacetamide-containing polymer and 5 to 40 parts by weight of alginic acid.

2. The care solution for contact lenses as claimed in claim 1, wherein the addition amount of the wetting agent is 0.01 to 0.2 parts by weight per 100 parts by weight of the buffer solution.

3. The care solution for contact lenses as claimed in claim 1, wherein the wetting agent further comprises a hyaluronic acid.

4. The care solution for contact lenses as claimed in claim 3, wherein the wetting agent further comprises 20 to 70 parts by weight of hyaluronic acid.

5. The care solution for contact lenses as claimed in claim 1, wherein the glycerol, vinylacetamide-containing polymer and alginic acid of the wetting agent can be added as a combination or individually into the buffer solution.

6. The care solution for contact lenses as claimed in claim 1, wherein the chelating agent is selected from the group consisting of ethylenediaminetetraacetic acid (EDTA) and the salt thereof, polyphosphates and the salt thereof, succinic acid and the salt thereof, tartaric acid and the salt thereof, and tetraacetic acid and the salt thereof.

7. The care solution for contact lenses as claimed in claim 1, wherein the surfactant is selected from the group consisting of sodium citrate, poloxamer, poloxamer derivatives, poloxamine, poloxamine derivatives, cationic surfactant and the combination thereof.

8. The care solution for contact lenses as claimed in claim 1, wherein the addition amount of the chelating agent is 0.01 to 1.0 parts by weight per 100 parts by weight of buffer solution.

9. The care solution for contact lenses as claimed in claim 1, wherein the addition amount of the surfactant is 0.1 to 1.0 parts by weight per 100 parts by weight of buffer solution.

10. The care solution for contact lenses as claimed in claim 1, further comprising disinfecting agents, antioxidants, thickeners, tonicity adjusting agents, lubricants or the combination thereof.

11. The care solution for contact lenses as claimed in claim 10, wherein the disinfecting agent is selected from the group consisting of polyhexamethylenebiguanide (PHMB), the water-soluble salts of PHMB, polyaminopropylbiguanide (PAPB), the water-soluble salts of polyaminopropylbiguanide, protamine sulfate and melittin.

12. The care solution for contact lenses as claimed in claim 10, wherein the antioxidant is selected from the group consisting of sulfite, ascorbate, butylated hydroxyanisole (BHA), butylated hydroxytoluene (BHT), astaxanthin and vitamin C and combinations thereof.

* * * * *